United States Patent [19]
Fotland et al.

[11] Patent Number: 5,454,257
[45] Date of Patent: Oct. 3, 1995

[54] METHOD OF DETERMINING WAX APPEARANCE POINT OF A COMPLEX REAL FLUID CRUDE LIQUID PETROLEUM COMPOSITION AND OF DETERMINING QUANTITY OF WAX PRECIPITATED THEREFROM

[75] Inventors: Per Fotland, Bergen; Knut Erik Grung, Mathopen, both of Norway

[73] Assignee: Norsk Hydro A.S., Oslo, Norway

[21] Appl. No.: 79,895

[22] Filed: Jun. 22, 1993

[30] Foreign Application Priority Data

Jun. 22, 1992 [NO] Norway .................................. 922469

[51] Int. Cl.⁶ .................................................. G01N 25/04
[52] U.S. Cl. ........................... 73/61.43; 73/61.46; 374/22; 374/16
[58] Field of Search .................... 73/61.43, 61.44, 73/61.46, 61.76, 64.41, 54.02, 64.54; 374/16, 22, 55, 56

[56] References Cited

U.S. PATENT DOCUMENTS

| | | | |
|---|---|---|---|
| 3,574,281 | 4/1971 | Casey et al. | 374/55 |
| 4,602,870 | 7/1986 | Rummel | 374/16 |
| 4,837,776 | 6/1989 | Poll | 374/56 |

FOREIGN PATENT DOCUMENTS

| | | |
|---|---|---|
| 1151510 | 4/1985 | U.S.S.R. . |
| 2046167 | 11/1980 | United Kingdom . |
| 2164160 | 3/1986 | United Kingdom . |

OTHER PUBLICATIONS

Abbott et al. "Scharm's Outline of Theory and Problems of Thermodynamics", N.Y. McGraw–Hill, p. 105, 1972.
Industrial and Engineering Chemistry, vol. 59, No. 10, Oct. 1967, R. H. Jacoby and L. Yarborough, "PVT Measurements on Petroleum Reservoir Fluids and Their Uses", pp. 48–62.
Chemical Abstracts, vol. 87, (1977), No. 154578/Izv. Vyssh, Uchebn. Zaved., (1977). 20(6), 52–56, E. A. Aleksandrova, A. P. Grishin, Y. Y. Lobachiov, "Temperature Research of Paraffins Phase Changes Using Dilatometric and Thermographic Methods".

Primary Examiner—Herzon E. Williams
Assistant Examiner—Michael J. Brook
Attorney, Agent, or Firm—Wenderoth, Lind & Ponack

[57] ABSTRACT

A wax appearance point in a petroleum produce is determined by measuring change in volume as a function of temperature. The appearance point appears as a deviation from a rectilinear graph. The quantity of wax which appears is determined by comparing a measured volume graph as a function of temperature with an estimated volume graph.

1 Claim, 3 Drawing Sheets

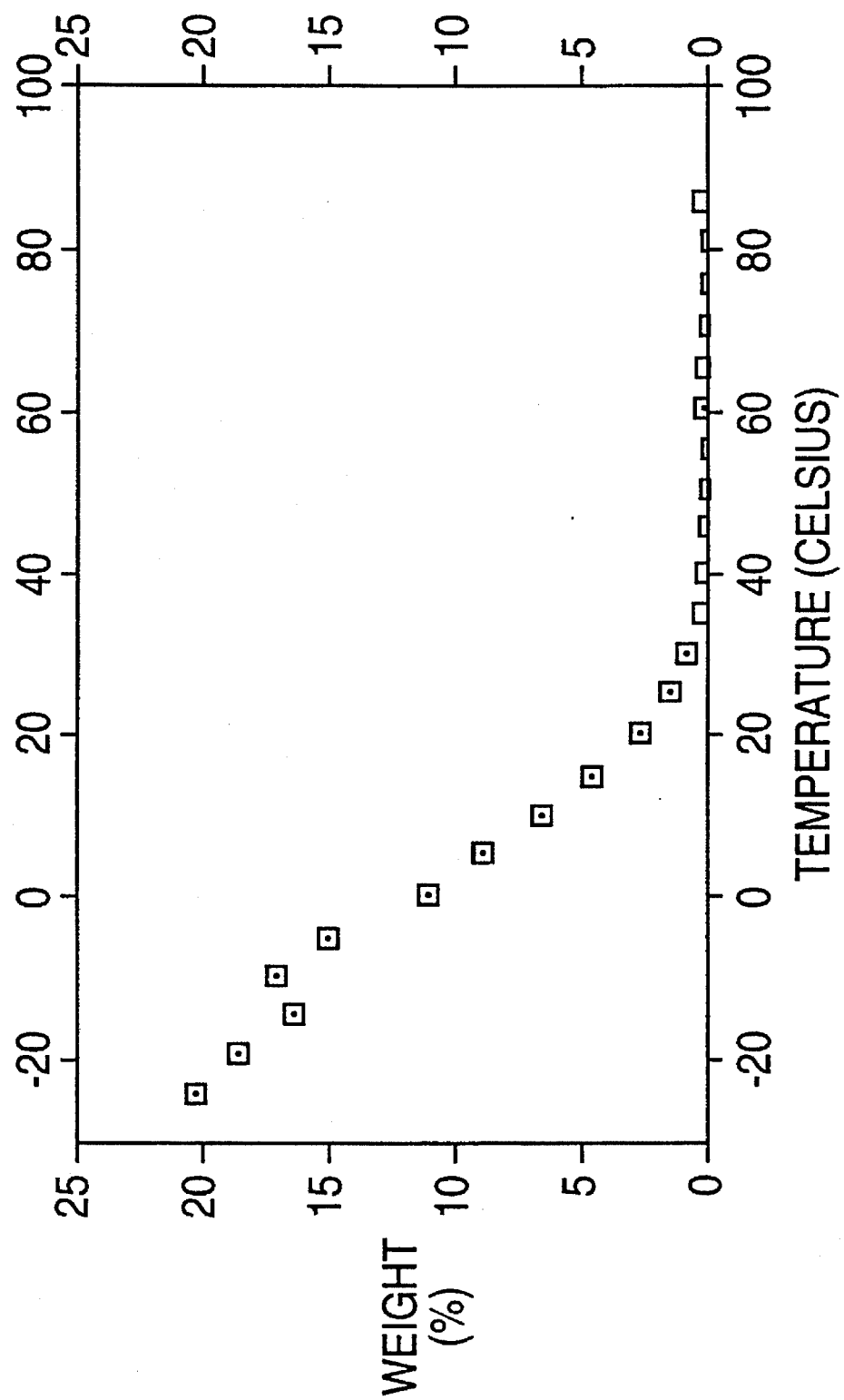

METHOD OF DETERMINING WAX APPEARANCE POINT OF A COMPLEX REAL FLUID CRUDE LIQUID PETROLEUM COMPOSITION AND OF DETERMINING QUANTITY OF WAX PRECIPITATED THEREFROM

BACKGROUND OF THE INVENTION

The present invention concerns a method for determining the wax appearance point and the quantity of wax in petroleum products.

Oil, or hydrocarbon fluid, has a complex composition and the number of individual components is so large as to be difficult to estimate in practice. A distinction is made between straight-chained paraffins (n-paraffins), branched paraffins (isoparaffins), naphthenes (cycloparaffins) and aromatic compounds. In addition, there are smaller quantities of compounds such as asphaltenes and resins. These are compounds which contain heteroatoms (oxygen, nitrogen and sulphur) as well as heavy metals. It is also important to distinguish between stabilized oil (without gas) and real fluid (with gas, such as occurs in a reservoir). The content of light hydrocarbons ($C_1$ to $C_6$) in real fluid is in the order of 20 mol % higher than for stabilized oil.

For the straight-chained paraffins, the change in physical properties is proportional with the increase in chain length. The branched paraffins have less predictable properties. An increasing level of branching will, in most cases, lead to a reduction in the boiling point and melting point. The content of the various paraffin isomers in a "normal" North Sea crude oil will be distributed in such a way that there is a majority of straight-chained paraffins and only small quantities of each individual isomer. The reasons for this are to be found in the geological origin of the oil, the conditions in the types of source rocks and the reservoir, as well as the large number of possible isomers with the same carbon chain length.

For wax appearance this means that good characterization of the appeared material is very difficult. The appearances will be concentrated in normal paraffins on account of the higher content of these components and due to the fact that the melting points for n-paraffins are considerably higher than for most other components in the oil. Models which are based on a wax fraction which is dissolved in the rest of the oil must therefore have a good analytical description of the composition of the complete fluid, in both its solid and liquid phase. With the analytical techniques which exist today this is not a realistic requirement.

The content of light components in the fluid will influence the solubility of the more long-chained components at a given temperature. In addition, an increase in pressure, as a function of an increased content of light components, will have an effect on the properties of the components in the oil and therefore also on solubility. The net effect of the increased pressure and the increased content of light components will therefore be dependent on the total composition.

Traditional methods for determining wax content in oil are "wax appearance point" by means of polarisation microscopy, "pour point" and UOP wax content.

Microscopy. A drop of oil (heated to 80° C.) is placed between two object-glasses. The oil is observed through a microscope (125×magnification). Polarized light is passed through the film of oil and further through a polarization filter which extinguishes all light. If crystals have been formed in the oil the polarized light is deflected and is not extinguished by the filter. This is observed through the microscope as luminous spots, corresponding to wax crystals. The method is dependent on the thickness of the wax film, the cooling speed (supercooling, equilibrium) and it is operator-dependent. Furthermore it is probable to assume that the composition of the oil will influence the level of supercooling and the equilibrium time for the formation of wax crystals. It is also generally preferable to use a system which measures the wax appearance point, WAP, by means of equilibrium and not by cooling at a given rate as this method describes. This method can only be used in stabilized oils.

Pour point. This method is carried out in accordance with ASTM D97-66 (1980 part 23). The pour point is defined as the temperature at which there is no movement in the sample when the sample bottle is held horizontally for five seconds. The sample is cooled from 80 degrees at a rate of 12 degrees C./hour and the pour point is checked every 2° C. This method gives a figure for the flow properties of stabilized oil.

UOP wax content. This method is described by Burger, E. D. et. al, J. Pet. Tech., 1981 (June), 1075–1086. The method is based on determining the components of the oil which are insoluble in acetone at −18° C. This is a definition of wax which is difficult to relate to the real wax content. Furthermore, it cannot be used for real fluid.

When designing development solutions for marginal oil fields (sub-sea solutions, etc.) it can be of decisive importance whether the effect of light components and increased pressure is positive or negative on the wax appearance point, the pour point and the quantity of wax as a function of temperature. This is because of the costs associated with the inhibition of wax, pigging facilities in the pipeline systems, insulation and any injection of solvents and hot oil. Furthermore, it will be of interest to know the temperature for gelling in connection with blocking the pipeline and any problems with starting up after such gelling. Wax deposits can also lead to problems in connection with inspection of pipelines for corrosion, etc.

Today there is no accepted method for determining the wax appearance point and the quantity of wax in real fluid.

SUMMARY OF THE INVENTION

On the basis of the above it was therefore desirable to develop a method for determining the wax appearance point and the quantity of wax under real pressure and gas saturation. The procedure which constitutes the present invention is based on phase changes in the fluid in connection with a change in temperature. This has the advantage that a change in the properties of the fluid is measured and can be directly explained by the transition from liquid to solid phase.

The method in accordance with the present invention can be used on fluids with the degree of saturation and pressure which are relevant in various field solutions. The effect of the changes in the fluid in connection with, for example, addition of an inhibitor or a mixture of different fluids in transportation pipelines, etc., can easily be studied.

The method for determining the wax appearance point in petroleum products in accordance with the present invention is characterized in that the wax appearance point is detected as the occurence of a deviation of a measured volume of a sample from a rectilinear temperature-volume graph defining volume changes of the sample due to expansivity thereof. Furthermore, the method for determining the quantity of wax which appears by measuring an amount of such deviation as a function of density of the wax. A pressure cell is placed in a thermostat bath, and a control unit for reading and setting pressure, temperature and the volume is connected to the pressure cell.

BRIEF DESCRIPTION OF THE DRAWINGS

The present invention will be described in more detail in the following by means of examples, with reference to the enclosed drawings, in which:

FIG. 4 is a diagram for determining the quantity of wax which appears, using data from FIG. 2.

DETAILED DESCRIPTION OF THE INVENTION

Figure 1:
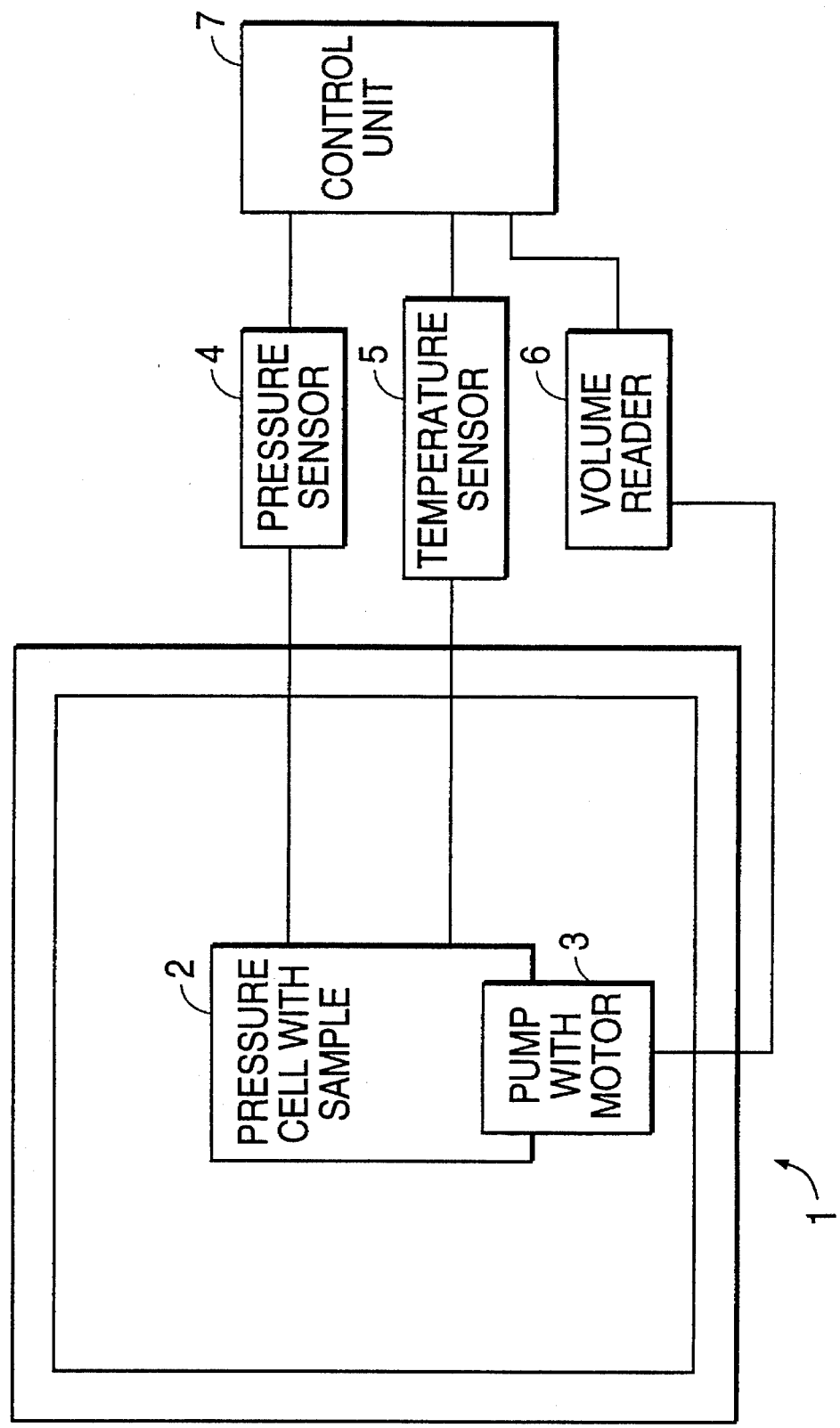
FIG. 1 is a schematic representation of the equipment employed in accordance with the present invention.

Equipment for carrying out the invention is represented in FIG. 1, in which reference numbers 1–7 respectively represent:

1. Thermostat bath, air.
2. Pressure cell with oil sample.
3. Pump, e.g. a piston pump, with motor to regulate pressure.
4. Pressure sensor.
5. Temperature sensor.
6. Volume reader.
7. Control unit for reading and setting pressure, temperature and volume.

If oil cools without the appearance of solid phases the oil will follow a normal exponential volume dependence on temperature. If the temperature interval is not too large it can be assumed that the thermal expansivity, $\alpha$, is constant and defined as usual:

$$\frac{1}{V}\left(\frac{\partial V}{\partial T}\right)_p = \alpha \qquad (1)$$

where V is the volume of the sample, T the temperature and $_p$ the constant pressure by derivation. This can be integrated in the usual way to produce the following equation:

$$V = V_0 e^{\alpha(T-T_0)} \qquad (2)$$

The integration takes place from $T_0$ to T which gives the volumes V and $V_0$.

By transferring an oil sample to a volumetrically calibrated pressure cell 2, setting the pressure to a given value and taking readings at equilibrium, the volume V can be followed as a function of the temperature T.

The appearance of a solid phase will cause the above equations no longer to apply for the whole system (solid+liquid). The system is then heterogeneous and the individual phases are best treated individually.

Solid crystalline phases usually have a greater density than the corresponding liquid phases. Therefore, with phase transitions of pure components a jump in volume occurs, measured against temperature. As described, oil is a mixture of many components and the conditions are therefore more complex. When the freezing point of some of the wax is reached, these components will precipitate. This causes a change in density which can, in turn, be observed as a change in volume beyond that described in the equations above.

In other words, from the wax appearance point down the change in volume will be due to two factors or elements: 1) expansivity of the liquid phase and 2) the difference in volume between the solid and liquid wax.

Figure 2:
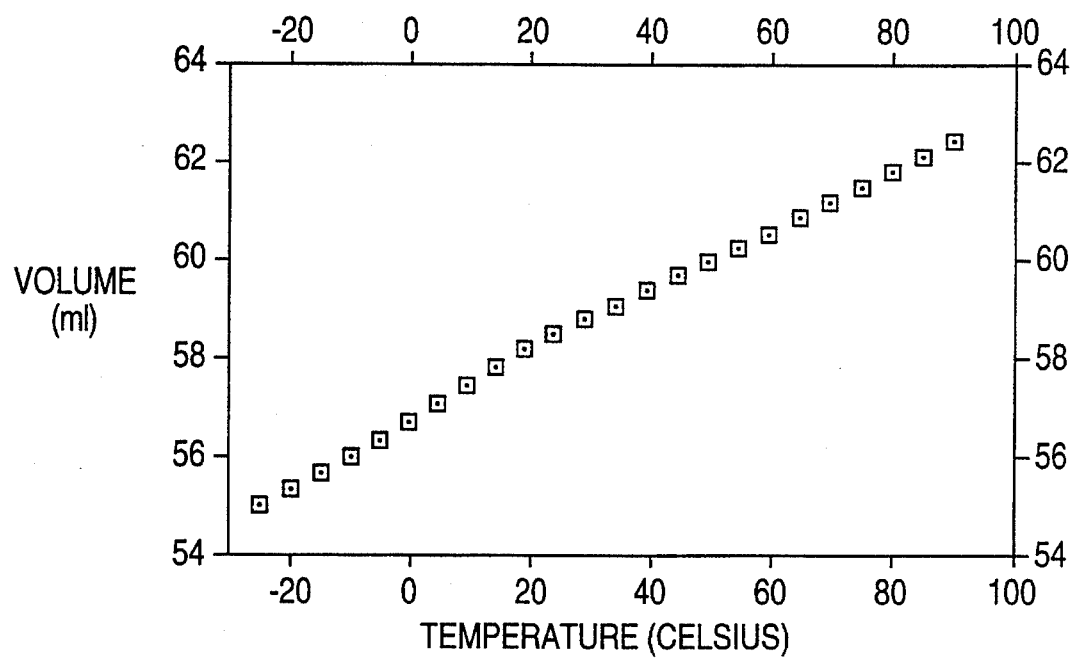
FIG. 2 is a diagram of a measured volume graph of an oil as a function of temperature.

Measurements show that appearances of wax can be detected by measuring the volume e.g. by sensor 6 detecting changes in position of the piston of pump 3, as a function of temperature at constant pressure. The change in volume can be divided into two elements as described above. The size of the element from the phase transition is dependent on the quantity of wax which appears per degree. FIG. 2 shows a measured volume graph for an oil. As can be seen, the volume change due to the phase transition is low but detectable.

All measurements were taken in an optical cell 2 as shown in FIG. 1, i.e. the whole sample volume was visible. The visually observed wax appearance point complied to a high degree with the volume observations. This crude oil was transparent with both laser light and normal light. The wax appearance could be observed as a strong increase in the dispersion of the light from the laser beam, and the precipitation was visible in normal light.

The wax appearance is thus determined by means of two independent methods and the results are in accordance with one another.

The simplest method for determining the appearance point is to linearize equation 2. Taking logarithms on both sides of the equation produces a straight line:

$$\ln V = \ln V_0 + \alpha(T-T_0) \qquad (3)$$

Figure 3:
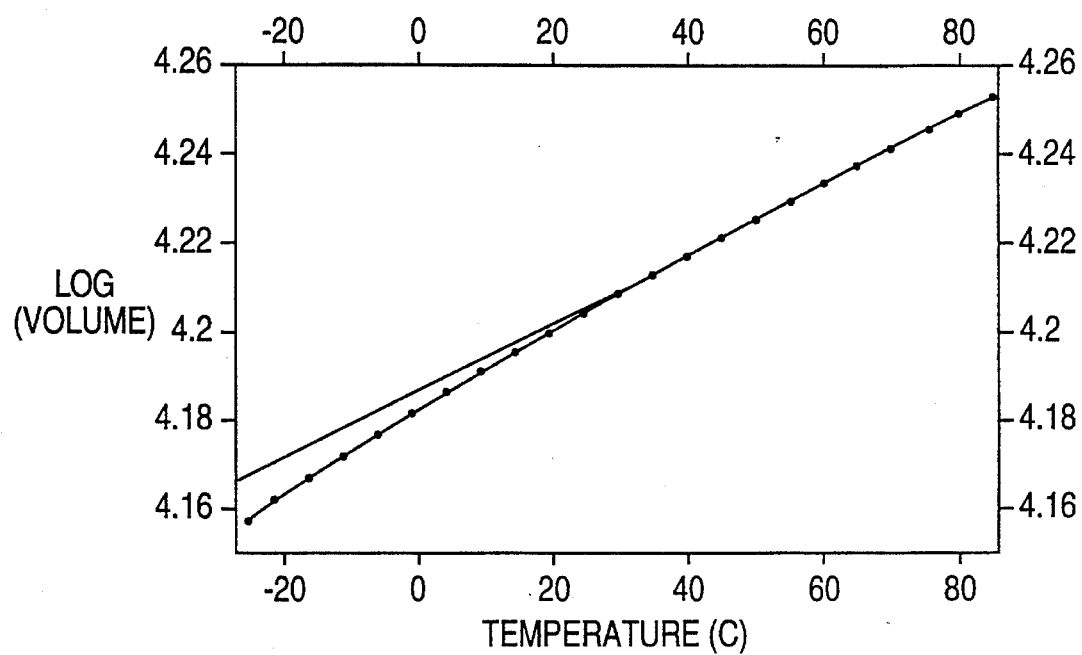
FIG. 3 is a diagram of the logarithm of the volume as a function of temperature using data from FIG. 2.

The measured quantities are V and T. A graph is plotted of lnV against T. If the oil does not contain appeared wax, the points will lie in a straight line. With wax appearance it will be possible to observe significant and systematic deviations from this line. This technique does not require that $V_0$ and $T_0$ be determined. Equation (3) can also be written:

$$\ln V = \ln V_0 - \alpha T_0 + \alpha T = \text{Const.} + \alpha T \qquad (4)$$

where $V_0$ and $T_0$ are combined in the constant. FIG. 3 shows the result of this procedure on data from FIG. 2. It is apparent that the appearance point is easier to observe in FIG. 3 than in FIG. 2.

By estimating the density of the solid and liquid wax and measuring the change in volume due to the phase transition, the quantity of wax which has appeared can be determined. FIG. 4 shows a result of this procedure. The density of the liquid wax in the mixture is difficult to estimate. The results must therefore be used with caution.

We claim:

1. A method of determining a wax appearance point of a complex real fluid crude liquid petroleum composition including a complex mixture of wax components comprised of n-paraffins, cycloparaffins, branched paraffins and aromatic compounds and asphaltenes and resins, said method comprising:

placing a sample of said liquid petroleum composition within a cell maintained at a constant pressure;

sequentially lowering the temperature of said sample, during which volume of said sample varies due to expansivity thereof until reaching a wax appearance point at which a wax component undergoes a phase change from liquid to solid, and after which volume of said sample varies as a function of expansivity thereof and a volume difference between solid and liquid wax;

measuring the volumes of said sample at respective lowering temperatures thereof;

detecting the occurrence of a wax appearance point by determining deviation of a measured volume from a rectilinear temperature-volume graph defining volume changes of said sample due to expansivity $\alpha$ thereof according to $$\alpha = [\ln(V/Vo)]/T$$

wherein:

T = temperature when taking a volume measurement,

V = measured volume at T, and

Vo = a starting volume; and determining the quantity of wax precipitated at the wax appearance point as a function of density of said wax, and a measured amount of said deviation.

* * * * *